(12) United States Patent
Dietrich et al.

(10) Patent No.: US 9,039,419 B2
(45) Date of Patent: May 26, 2015

(54) METHOD AND SYSTEM FOR CONTROLLING SKILL ACQUISITION INTERFACES

(75) Inventors: Brenda Dietrich, Yorktown Heights, NY (US); Jennifer Lai, Garrison, NY (US); Yan Liu, Elmsford, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 793 days.

(21) Appl. No.: 12/614,175

(22) Filed: Nov. 6, 2009

(65) Prior Publication Data
US 2011/0111384 A1 May 12, 2011

(51) Int. Cl.
G09B 19/00 (2006.01)
G09B 7/00 (2006.01)
A61B 5/16 (2006.01)
A61B 5/18 (2006.01)

(52) U.S. Cl.
CPC ... *G09B 7/00* (2013.01); *A61B 5/16* (2013.01); *A61B 5/18* (2013.01); *G09B 19/00* (2013.01)

(58) Field of Classification Search
CPC .......... A61B 5/16; A61B 5/161; A61B 5/162; A61B 5/18; G09B 19/00
USPC ............................ 434/38, 236, 323, 362, 350
See application file for complete search history.

(56) References Cited

U.S. PATENT DOCUMENTS

| | | | |
|---|---|---|---|
| 5,731,805 A * | 3/1998 | Tognazzini et al. | 345/156 |
| 6,320,976 B1 * | 11/2001 | Murthy et al. | 382/128 |
| 7,719,520 B2 * | 5/2010 | Singh et al. | 345/169 |
| 2004/0175684 A1 * | 9/2004 | Kaasa et al. | 434/262 |
| 2011/0091847 A1 * | 4/2011 | Carroll et al. | 434/236 |
| 2011/0105859 A1 * | 5/2011 | Popovic et al. | 600/301 |

OTHER PUBLICATIONS

P. Kasarskis et al., Comparison of Expert and Novice Scan Behaviors During VFR Flight, Presented at the 11th International Symposium on Aviation Psychology, Columbus, OH: The Ohio State University, 2001.
Rabiner, "A Tutorial on Hidden Markov Models and Selected Applications in Speech Recognition", Proceedings of the IEEE, vol. 77, No. 2, Feb. 1989, pp. 257-286.

* cited by examiner

*Primary Examiner* — Peter Egloff
(74) *Attorney, Agent, or Firm* — Scully, Scott, Murphy & Presser, P.C.; Daniel P. Morris, Esq.

(57) ABSTRACT

A method and system for capturing expert behavior that the expert is not even necessarily conscious of, such as gaze patterns, that are tied to positive outcomes, and to create a catalog (e.g. database) of these behaviors. The system compares the current behavior of a person, for example a novice, against this catalog of expert behaviors. If the current behavior is significantly different, the system would adapt various aspects of the interface to bring the current behavior closer in line to that of the expert.

12 Claims, 4 Drawing Sheets

METHOD AND SYSTEM FOR CONTROLLING SKILL ACQUISITION INTERFACES

BACKGROUND OF THE INVENTION

1. Field of the Invention

This invention generally relates to the field of knowledge management, and more specifically to a system and method for controlling skill acquisition, e.g. the transfer of skills from an expert to a novice, using gaze scanning behavior through a user interface.

2. Background Art

The gap in organizational knowledge that is created when an expert retires or leaves an organization is a problem that has been studied in the field of knowledge management for many years. Prior solutions have required the expert to specify everything he does in a given area or for a given task. The resulting document is then stored for others to read. One of the primary obstacles to the transfer of knowledge from an expert to a novice is that tacit knowledge is not something that experts are able to specify since they are often not even aware of how or why they do things a certain way. Secondly experts think in more abstract concepts than novices, thus their explanations can be hard for novices to assimilate. Lastly, knowledge is not easily acquired by reading a document.

Most gaze tracking devices, such as SensoMotoric® or ™ manufactured by SensoMotoric Instruments and faceLAB® manufactured by Seeing Machines, operate based upon the principal that the direction of a person's gaze is directly related to the relative positions of the pupil and the reflection of an object off the cornea (gaze tracking is often termed "eye tracking"). These devices often include image processing capabilities that operate on a video image of an eye to determine the gaze direction of the eye. These image processing capabilities are enhanced by using the bright eye affect.

The bright eye affect is a result of the highly reflective nature of the retina. This characteristic of the retina means that a significant amount of the light that enters an eye is reflected back through the pupil. Thus, when light shines into an eye along the axis of a camera lens, the retina reflects a significant portion of the light back to the camera. Hence, the pupil appears as a bright disk to the camera. This affect allows the pupil to be more readily imaged from a video of an eye.

Other systems and methods exist for gaze tracking. Some systems implement two video cameras, one for tracking head movement and the other for measuring a reflection off of the eyes. Other mechanisms involve measuring electric potential differences between locations on different sides of an eye. High accuracy devices are very intrusive on the user and require that the user's head be held in a fixed position or that the user wear special equipment to track the eye.

Recently, an eye gaze eye tracking system has been developed as described in The Eyegaze Eyetracking System—Unique Example of a Multiple-Use Technology, 4th Annual 1994 IEEE Dual-Use Technologies and Applications Conference, May, 1994. This system comprises a video camera located below a computer display that monitors one of the user's eyes. The device also contains an infrared light emitting diode (LED) located at the center of the camera's lens to maximize the bright-eye affect. Image processing software on the computer computes the user's gaze point on the display sixty times a second with an accuracy of about a quarter inch.

Gaze tracking devices have been used for weapon control, operator training, usability analysis, market research, and as an enablement for the disabled. However, gaze patterns and reacting to gaze in a user interface have not been applied together in an adaptive user interface for the purpose of skill acquisition.

The idea of analyzing gaze patterns for differences between novices and experts is not novel. Kasarskis et al. 2001 showed differences in performance and eye movements between expert and novice pilots who performed landings in a flight simulator. Additionally, other studies have shown that differences exist between expert and novice gaze patterns in the following areas: radiology, basketball, airplane piloting.

There is prior art in using gaze in accessibility systems for "selection" when the user has physical motor impairments.

However, these two concepts of differences in gaze patterns and reacting to gaze in a user interface have not been applied together in an adaptive user interface for the purpose of skill acquisition. It would be highly desirable to provide a novel system and method for controlling skill acquisition interfaces that captures what an expert does through recognition technologies (e.g. eye tracking), storing the implicit data, and then adjusting the interface for a novice based on deviations from this standard.

SUMMARY OF THE INVENTION

It is an object of the present invention to provide a system and method for training a novice so that the novice may learn to "look" at things in the manner as an expert in the field does.

It is a further object of this invention is to provide a novel system and method to identify a test object, identify a reference pattern derived from the test object, provide an output display, said display correlating differential and comparative reference patterns with reference to the test object, and correct differences in said patterns using a user interface.

More particularly, this invention is a novel system and method for controlling skill acquisition, e.g., enabling the transfer of skills from an expert to a novice. This invention creates technology to support the problematic transfer of skills from an expert to a novice. This invention is inspired by the "apprenticeship model" of working side-by-side or watching over the shoulder of an expert. However, real shadowing of an expert is expensive (1 to 1 relationship) and not always possible if the expert is no longer available. Technology can make this relationship 1 to N, asynchronous, and remote.

Thus, in one aspect, the present invention is directed to a system and computer-implemented method for controlling skill acquisition interfaces via a user interface, the method comprising the steps of:

tracking and storing attributes of behavior of one or more first users when performing a task;

analyzing attributes of behavior of said one or more first users performing said task and associating behavior patterns of said one or more first users' with significant outcomes;

tracking a second user's behavior when subsequently performing the same task as said one or more first users;

comparing, in real time, said second user's behavior patterns with said stored attributes of first user's behavior tied to said significant outcomes;

detecting, in real time, differences between said second user's behavior patterns and said first user's behavior; and providing indication for correcting any said detected differences commensurate with said significant outcomes via said user interface such that said second user acquires skills as said first user.

Further to this aspect of the invention, the step of analyzing attributes of behavior of said one or more first users performing said task includes implementing a machine learning algorithm, said significant outcomes comprising positive or negative outcomes in performing the task.

Thus, in one exemplary, but non-limiting environment, attributes of expert behavior (e.g., behavior that the expert is not even necessarily conscious of, such as gaze patterns), and a catalog (e.g. database) of these behaviors is created. Then, the system compares the current behavioral attributes of a person, for example, a novice, against this catalog of machine learned expert behaviors. If the current novice's behavior is significantly different and analyzed as being tied to negative outcomes, for example, if the gaze scanning behavior as performed by said novice is different than the skills behavior as the expert, the system adapts various aspects of the interface to bring the current novice's behavior closer in line to that of the expert.

Thus, according to a further aspect of the invention, there is provided a computer-implemented method for controlling skill acquisition interfaces comprising the steps of tracking and storing first reference patterns associated with one or more first users when viewing an image via a user interface;

analyzing attributes of viewing behavior pattern of said one or more first users performing said task and associating said behavior patterns of said one or more first users' with significant outcomes;

tracking second reference patterns of a second user when subsequently viewing a same image as the first user;

comparing, in real time, the second reference patterns of the second user with the stored first reference patterns of the one or more first users tied to said significant outcomes;

detecting, in real time, differences between the stored first reference patterns and the second reference patterns; and providing an indication via the user interface for the second user to correct viewing of the image commensurate with said significant outcomes, whereby the second user acquires skills as the first user.

According to a further aspect of the invention, there is provided a system for controlling skill acquisition interfaces, the system comprising:

means for tracking attributes of behavior of one or more first and second users when performing a task, and associating the behavior patterns of the one or more first users' with significant outcomes of the task;

storage device for storing attributes of behavior of the one or more first users, and respective associated significant outcomes of the task, means for comparing, in real time, attributes of the second user's behavior when subsequently performing the same task as the first user with the stored attributes of the one or more first users' behavior tied to the significant outcomes, the means further detecting differences between the first user's attributes of behavior patterns and the second user's attributes of behavior; and means associated with the user interface for providing an indication for the second user to correct any the detected behavioral differences commensurate with the significant outcomes such that the second user acquires skills as the first user.

Advantageously, the novel system and method for controlling skill acquisition interfaces that captures what an expert does is applicable to many recognition technologies, including, but not limited to: handwriting recognition, speech recognition and gesture recognition.

Further benefits and advantages of this invention will become apparent from a consideration of the following detailed description, given with reference to the accompanying drawings, which specify and show preferred embodiments of the invention.

DETAILED DESCRIPTION OF THE PREFERRED EMBODIMENTS

The present invention is directed to a system and computer-implemented method for controlling skill acquisition interfaces via a user interface. One embodiment is described herein is in the context of eye pattern gazing recognition technology. However, the present invention is adapted for use with many other recognition technologies including, but not limited to: handwriting recognition, speech recognition and gesture recognition.

Figure 1:
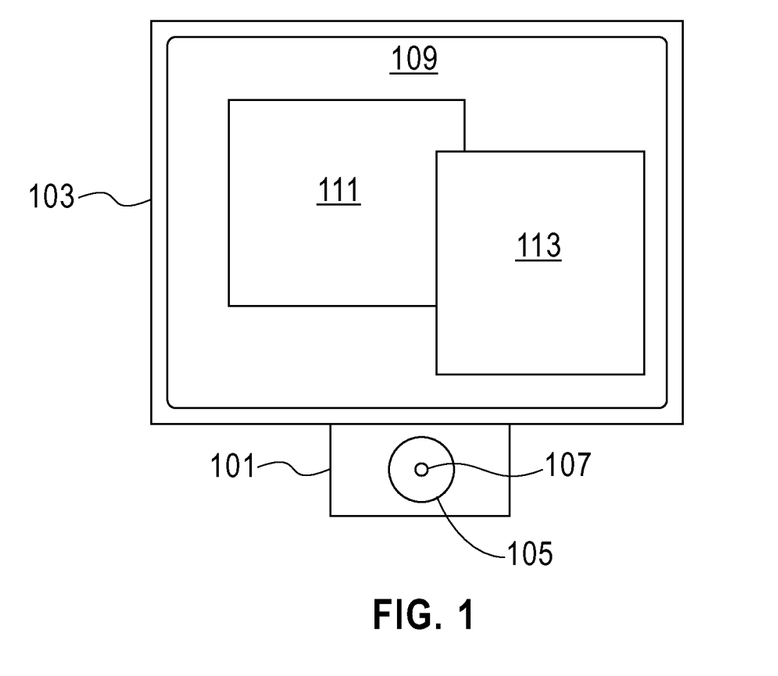
FIG. 1 illustrates a display device fitted with gaze tracking equipment according to one aspect of the invention.

FIG. 1 illustrates a gaze tracking device 101 attached to a computer display device 103. As illustrated, the gaze tracking device 101 is mounted below the computer display 103 and in one embodiment, comprises a video lens 105 for real-time video capture, with an infrared LED 107 mounted on the center of the lens 105. One skilled in the art will understand that one of many different types of gaze tracking devices can be used and mounted in various positions according to the invention. The computer display device 103 has a display area 109 that the computer can access to display information. The computer generally creates a plurality of windows 111 and 113 for this informational display. The expert user gazes images that are formed on the display. As the expert user looks at the display area 109, the gaze tracking device determines behavioral attributes, e.g., the user's gaze position when viewing the image, represented as one or more gaze "coordinates" relating to the displayed user interface. The gaze coordinate is an ordered pair of values providing the immediate two-dimensional coordinates of where the user's gaze is positioned on the screen display. A number of gaze coordinates can be used to develop a gaze position that is a two dimensional coordinate of a time weighted average of the gaze coordinates. The invention need not have precise gaze coordinates, however, the gaze coordinates tolerance must be accurate to at least approximately a ¼ inch. One skilled in the art will understand that the gaze position could be displayed via the user interface as a rectangle, polygon, circle or other shape representing an area of interest. Further one skilled in the art will understand that the gaze tracking device 101 may be configured to provide the gaze position only when the expert user has shown interest in a displayed area for a sufficient time, or that application or system program logic may be utilized to detect when the user has shown an interest by monitoring the gaze coordinates over some period of time. The gaze position is developed when the system detects that the user has become interested in a particular area of the display. The system detects this condition by recognizing that the expert user's gaze has been limited to a particular region of the displayable area 109 for a period of time. These particular gaze patterns will be transferred from expert to novice, as will be explained below.

Figure 2:
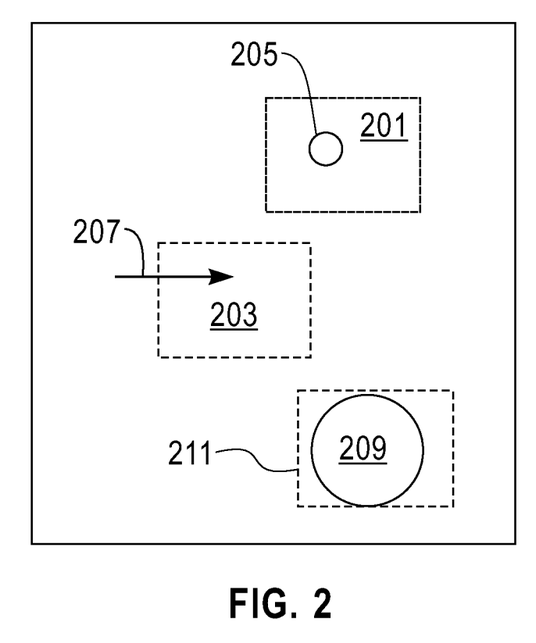
FIG. 2 illustrates aspects of a gaze position.

FIG. 2 illustrates aspects of a gaze position determined from gaze coordinates returned from a gaze tracking device 101 of FIG. 1. The dashed rectangle labeled as 201 indicates the boundaries of a displayed image (not shown). Because the gaze tracking device has an inherent tolerance and because the user's gaze constantly moves (because of involuntary eye movements) even when focused on an area of interest, this embodiment of the invention provides the gaze position as an area 205 where the user's gaze is fixed. The provided area 205 indicates that the user's gaze did not leave the specified area for a given time, e.g., a half second. The application program that uses the returned circular area 205 is able to determine that the user's gaze is well within the image 201 because the provided circle is completely contained within the area of the image. If the user has interest in the entire image, the gaze would be more diffused resulting in a larger circle. For example, in comparing the image labeled 201 with an image 211, the user viewing the image 201 has focused in on a particular aspect of the image as indicated by the circle labeled as 205. The user viewing the image 211 has indicated more interest in the totality of the image as compared to a particular aspect of the image as indicated by the circle labeled as 209. One skilled in the art will understand that a rectangle or other area indication can be used as well as a circle. Again, these particular gaze patterns will be transferred from expert to novice, as will be explained below.

In another embodiment of the invention, the gaze tracker device 101 of FIG. 1 returns the gaze position as a point. For example, a dashed rectangle labeled as 203 in FIG. 2 indicates the boundaries of a different displayed image (again this image is not shown). In this embodiment, the gaze tracker, after processing gaze movements over some period of time, simply returns a point that is a time weighted average of the position of the gaze. This point is indicated by the arrow labeled as 207 in FIG. 2.

Figure 3:
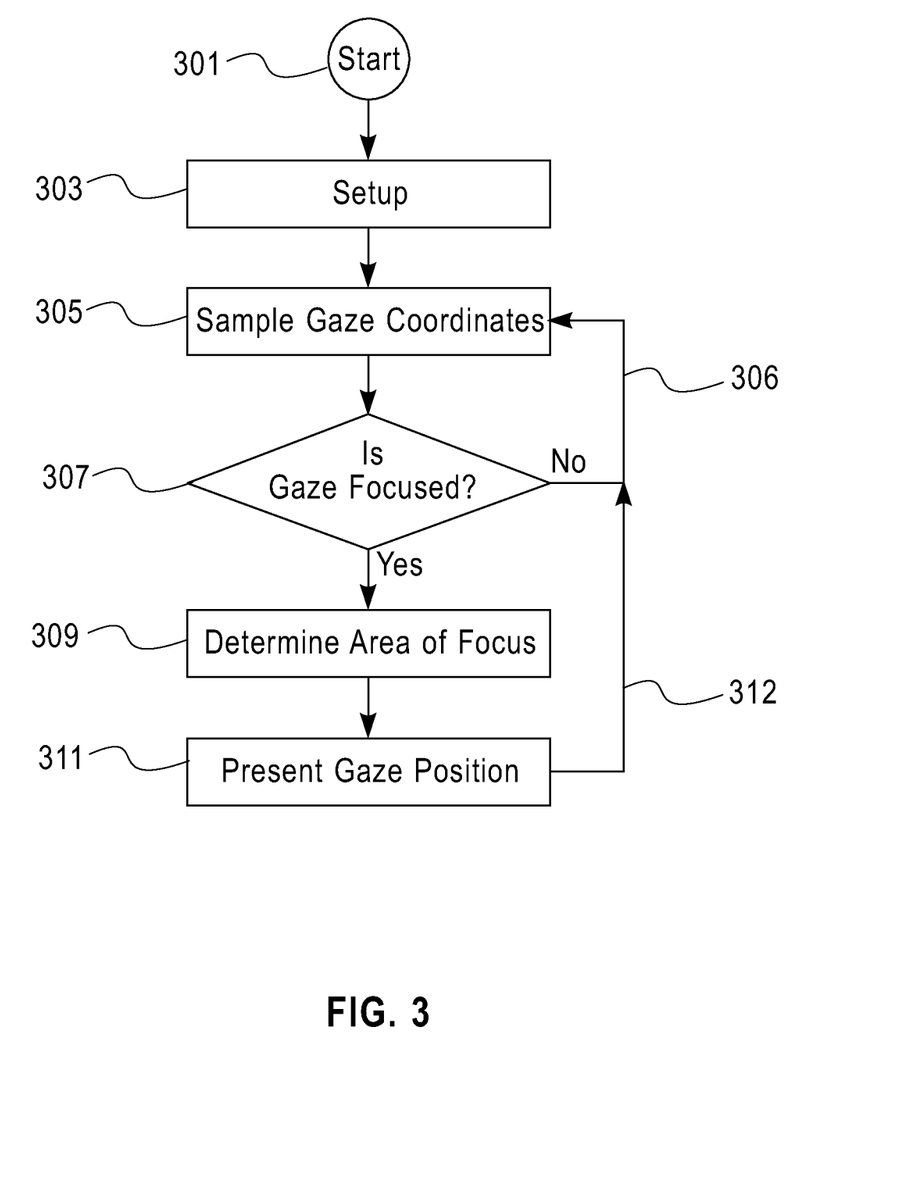
FIG. 3 illustrates the process for determining a gaze position.

FIG. 3 illustrates the process used to develop a gaze position from a plurality of gaze coordinates provided via a computer device's user interface. The process starts at a terminal 301. Next at a step 303, the process performs any necessary setup or initialization steps. This includes initializing timer program logic to periodically gather instantaneous gaze coordinate data from the gaze tracker apparatus, acquiring user preference data and other one-time initializations. Next at a step 305, the process receives a plurality of gaze coordinates. These gaze coordinates indicate the position of the user's gaze over a given time. After a sufficient number of gaze coordinates are gathered, the process examines the gaze coordinates for a focus pattern at a branch point 307. A focus pattern occurs when the gaze coordinates are all within some boundary without gaze coordinates being statistically far from the others. If the gaze coordinates do not show a focused gaze, the gathering of instantaneous gaze coordinates continues as shown by an arrow 306. If, at the branch point 307 a focus pattern is found, then a step 309 determines an area of focus that contains the statistically significant gaze coordinate(s). Finally, in a step 311 the gaze position is made available to the program logic for use. Finally, the process repeats as shown by an arrow 312 by returning to step 305 for receiving new gaze position coordinates. In the case where the gaze position is presented as an area instead of a simple coordinate pair, the receiving program logic determines which view is overlapped by the gaze position.

There are various well known methods in the art to present the gaze position to program logic such as an application program. These include but are not limited to: providing an exception to an application, and sending an interprogram message containing the gaze position to the application.

Figure 4:
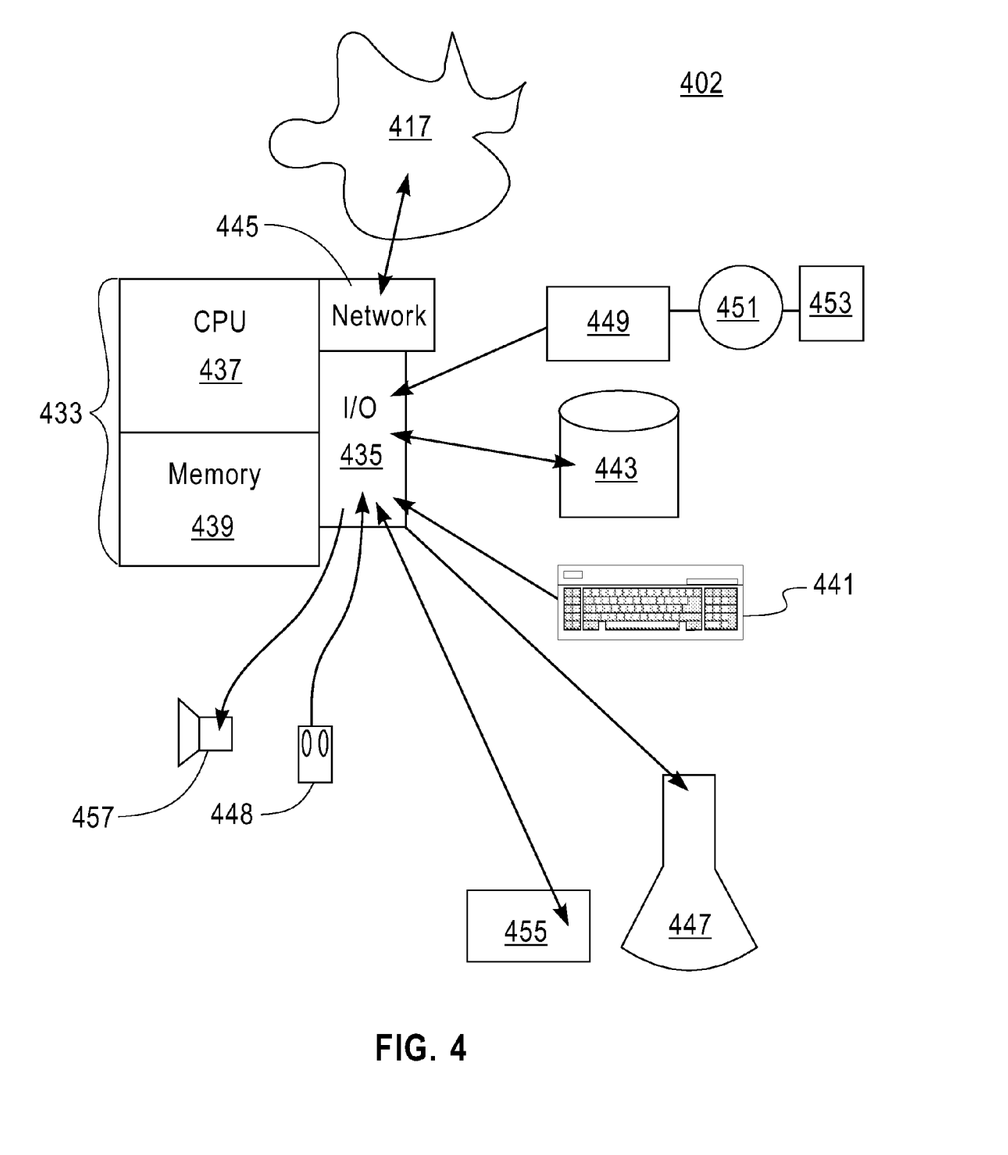
FIG. 4 illustrates a portion of a computer system, including a CPU and a conventional memory in which the present invention may be embodied.

FIG. 4 illustrates a computer system referenced to by the general reference character 402, configured to support the invention. The system 402 includes a processor 433 having an Input/Output ("I/O") or user interface section 435, a central processing unit ("CPU") 437 and a memory section 439. The I/O or user interface section 435 is connected to a keyboard 441, a disk storage unit 443, a network interface 445 to provide access to a network 417, a display unit 447, a pointing device 448, a gaze-tracker device 455, a speaker 457 and a CD-ROM drive unit 449. The CD-ROM unit 449 can read a CD-ROM medium 451 that typically contains a plurality of programs 453 and data. The CD-ROM 449 and the disk storage unit 443 comprise a file storage mechanism. One skilled in the art will understand that the file storage mechanism may comprise read only memory, RAM or other storage technology that allows a computer to access data. Such a computer system is capable of executing programmed logic that embodies the invention.

An important characteristic of modern computing systems is the interface between the human user and the computer. Modern computer systems use a graphical user interface (GUI) to simplify the interaction between a user and a computer. A GUI equipped computer communicates with a user by displaying graphics, including text and icons, on a display screen and the user communicates with the machine both by typing in textual information in response to dialogs and by manipulating the displayed icons with a pointing device, such as a mouse.

One characteristic of a GUI between the human user and the computer found, for example, on a modern computing system, is that the GUI is only responsive to a user's explicit manipulation of the pointing device or keyboard. In the case of a mouse, the user physically moves the mouse device and a cursor on the display moves accordingly. Some pointing devices actually track the user's gaze and move the cursor to where the user "looks" on the display screen. However, even with the gaze tracking (eye tracking) devices, the GUI only responds to the user's explicit commands whether that command be a button press, a blink, or a shift of view. The computer remains a tool that the user operates by issuing explicit commands.

Skill Acquisition from Expert to Novice

According to the invention, in the embodiment of gaze pattern recognition technologies as depicted herein for non-limiting, exemplary purposes, the gaze patterns of expert behavior are first captured when that expert is viewing an image or performing a task via a GUI. Subsequent, as part of the invention, the gaze patterns of a novice performing the identical task via the GUI, are compared to the prior captured and stored gaze patterns of the expert via the GUI when viewing the same image. The differences between both gaze patterns are determined by well-known machine learning algorithms which differences are associated with significant outcomes (positive or negative outcomes) in real time.

In one embodiment, machine learning implements hidden markov model and state-duration hidden markov modeling techniques. In these techniques, "sequential" patterns of eye gaze location and eye gaze duration are tracked. A hidden markov model is built for experts and one is built for novices to capture the different behaviors. Then, a Naive Bayes-like classifier may be trained to predict the labels (experts or novices) for a new eye-gaze sequence. Detailed description of hidden markov model and state-duration hidden markov models and selected applications in speech recognition can be found in Rabiner, L. R. Proceedings of the IEEE.

Any differences that are detected between the gaze patterns as determined by well-known machine learning algorithms are also compiled into a database of differences that is stored in disk storage unit 443 in FIG. 4. The database, which is maintained for associated images or tasks, is a catalog of all the differences in behavior between the expert and the novice. The two primary aspects that would be watched for comparative purposes, in one example embodiment, are the differences in location (where the gaze is fixated) and duration (how long a given area gets attention), although the tracking of the gaze path may also be performed.

More particularly, the detection of differences in gaze patterns, in accordance with an example embodiment, is implemented by machine learning technologies that implementing techniques (machine learning methods, e.g., supervised or unsupervised learning) to extract rules and patterns out of data sets (e.g., prior experts' gaze pattern training data) and associate these patterns and rules with significant (i.e., positive or negative outcomes). This prior-implemented machine learning step tracks each one or more expert's behavior for a given task, e.g., viewing images, and ties the expert's behavior with either a successful (positive) or negative outcome which are maintained by the system. Then, subsequently, for a new Novice N viewing the same image type or performing similar behavior, the novice behavior patterns are tracked, e.g., by gaze tracking devices in the example implementation; and, in real-time, an analysis is performed against the machine learned trained data sets to detect for any difference in the novice behavior patterns. For example, it is determined whether the detected gaze location/duration differences are tied to one or more positive or negative outcomes of the machine learned trained data sets (e.g., one or more experts' recorded gaze pattern training data). Finally, the display is modified, in real-time, accordingly in order to correct, if necessary, the novice's behavior (e.g., if behavior is detected as tied to negative outcomes). Thus, in the example described provided, the display will indicate to user if that novice's behavior needs to change (e.g., novice's gaze pattern needs to be re-redirected, tracked along another path, alter duration of an area upon which a gaze is to be fixated)).

As mentioned, the correction of differences is performed via a user interface, in accordance with a preferred embodiment. The goal is to train the novice so that they learn to "look" at things the way an expert does. Therefore, if it is detected by gaze tracking device that there is a given area of the object being displayed on the screen (e.g. medical radiographic film, airport x-ray image, seismographic image) that gets significant attention from an expert and is not being viewed in a similar way by the novice, the system generates a display to draw the gaze pattern of the novice closer to that of the expert. This could be done in the following ways: by movement of the image, by effecting color change of the displayed image or by effecting intensity change in the displayed image. It is understood that additional ways for aligning a novice's gaze pattern to that of the expert's are contemplated (e.g., play back of an audio instruction/command).

Figure 5:
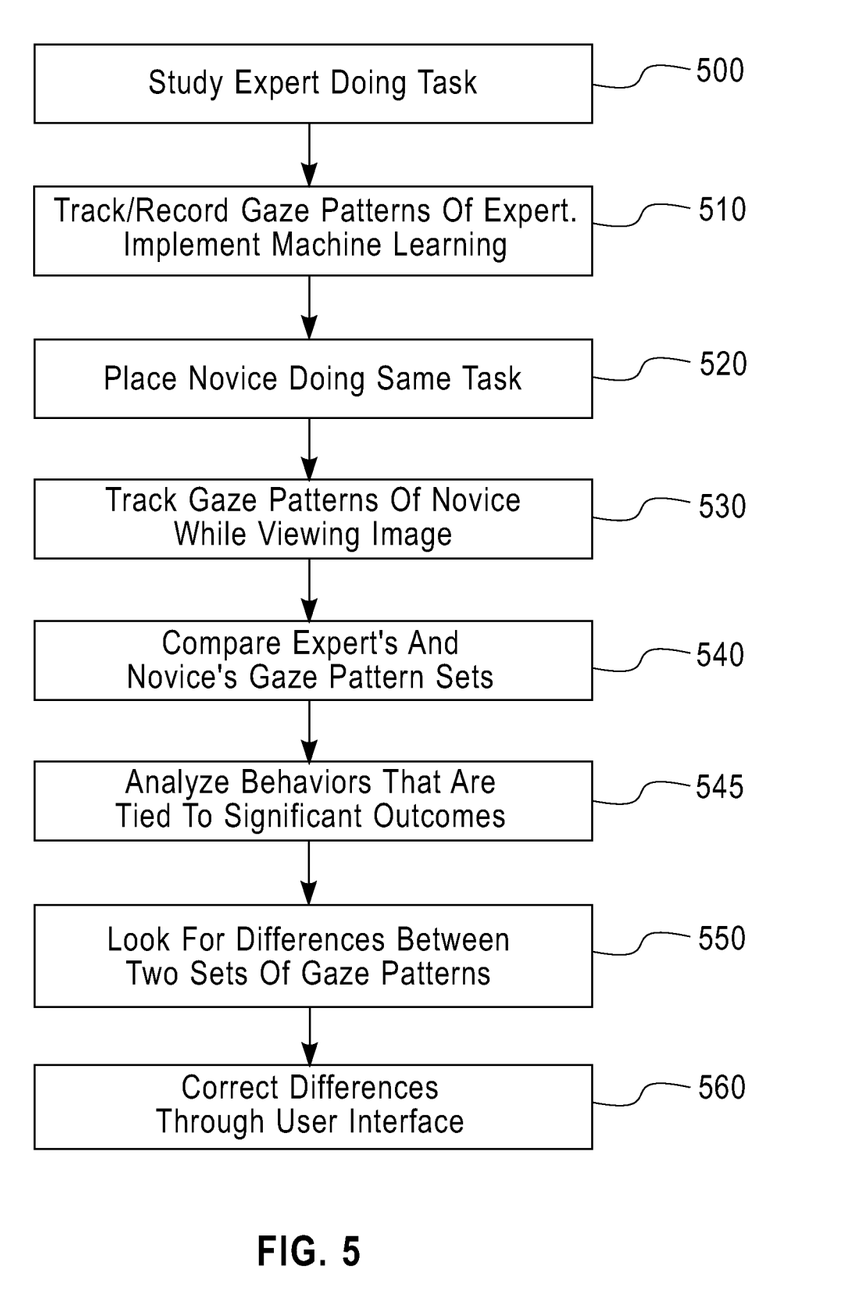
FIG. 5 illustrates a flowchart describing the comparison between the gaze patterns of an expert and the gaze patterns of a novice, in accordance with a preferred embodiment.

FIG. 5 illustrates a flowchart describing the process for comparing the gaze patterns of an expert and the gaze patterns of a novice, in accordance with the example embodiment of the invention employing eye (gaze pattern) tracking technology for skills acquisition. In a first step 500, there is performed the gaze tracking of an expert performing a task, for example a radiologist examining a displayed image, that may be video, audio or text. The gaze patterns of the expert are tracked, using eye-tracking technology at step 510. This step includes the implementation of machine learning wherein the behavior patterns, i.e., experts recorded gaze patterns for the same image (e.g., with respect to gaze location/duration of the viewed image and/or other attributes) are tied to significant outcomes. Then, subsequently, after the expert's gaze patterns are captured, a novice performs the same task 520 (e.g., gazes at the same image) and, in real-time, the novice's gaze patterns are tracked for that same image at step 530. The two sets of gaze patterns are further compared at step 540 and at step 545, the detected differences are analyzed for behavior that are tied to significant outcomes via the machine learning algorithms employed. Then, at step 550, differences between the two sets are determined and a database of these differences may then be created. The system thus tracks a novice's gaze pattern of that particular image while working and compares the novice's tracked gaze pattern to the database of captured and stored expert gaze patterns. When a deviation occurs, i.e., a gaze pattern is not fixated at an area that needs attention, or the gaze pattern indicates viewing along an incorrect path, e.g., a "negative" outcome, it is corrected through the user interface at step 560. The correction of differences may be implemented via the GUI by creating movement of the image, color change of the image or intensity change in the image, individually, or in combination, to help facilitate the promotion of novice behavior to expert level of behavior.

As will be readily apparent to those skilled in the art, the present invention can be realized in hardware, software, or a combination of hardware and software. Any kind of computer/server system(s)—or other apparatus adapted for carrying out the methods described herein—is suited. A typical combination of hardware and software could be a general purpose computer system with a computer program that, when loaded and executed, carries out the respective methods described herein. Alternatively, a specific use computer, containing specialized hardware for carrying out one or more of the functional tasks of the invention, could be utilized.

The present invention, or aspects of the invention, can also be embodied in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

While it is apparent that the invention herein disclosed is well calculated to fulfill the objects stated above, it will be appreciated that numerous modifications and embodiments may be devised by those skilled in the art, and it is intended that the appended claims cover all such modifications and embodiments as fall within the true spirit and scope of the present invention.

What is claimed is:

1. A computer-implemented method for acquiring skills comprising the steps of:

tracking, using a gaze tracking device having a lens for real-time video capture, attributes of a viewing behavior of one or more first expert users when performing a task and storing said attributes of said viewing behavior in a memory storage device associated with a processor device, said attributes of viewing behavior comprising a user's gaze pattern including: locations where a viewing gaze is fixated, a gaze duration at said locations, a gaze path being tracked, and a location representing a weighted average of a plurality of gaze positions whose weights are associated with corresponding time values;

tracking, using said gaze tracking device, said attributes of a viewing behavior of one or more second novice users when performing the task and storing said attributes of said novice user's viewing behavior in a memory storage device associated with a processor device;

implementing a machine learning algorithm to learn differences between said attributes of viewing behavior of said one or more first expert users performing said task and said attributes of viewing behavior of said one or more second novice users performing the task and associating said learned differences with significant positive or negative outcomes of said task;

storing in said memory storage a catalog of said learned differences for the task that are tied to said significant outcomes; and subsequently tracking, using said gaze tracking device, a further user's viewing behavior when subsequently performing the same task as said one or more first expert users;

comparing, in real time, attributes of said further user's viewing behavior with said stored attributes of said first expert user's behavior tied to said significant outcomes to detect real-time viewing behavior differences;

comparing, in real time, a detected difference against said catalog of stored learned differences that are tied to said significant outcomes; and providing an output indication for said further user to correct any said detected behavioral differences commensurate with said significant outcomes such that said further user acquires skills as said first expert user, wherein a processor coupled to a memory storage device is configured to perform the machine learning, the comparing to detect differences, the differences comparing, and the providing.

2. The method according to claim 1, wherein performing a task comprises viewing an image through a user interface.

3. The method according to claim 1, wherein the step of providing an output indication to correct detected behavioral differences comprises one or more of:

creating movement of a displayed image via said interface, changing color of said image via said interface and changing intensity of said image via said interface to align said second user's pattern with first reference patterns, or combinations thereof.

4. The method according to claim 1, wherein the step of providing an indication to correct detected behavioral differences includes providing an audio message for said second user to correct attributes of detected behavior.

5. A system for controlling skill acquisition interfaces, the system comprising:

at least one memory storage device;

at least one processor coupled to the at least one memory storage device, and a gaze tracking device having a lens for real-time video capture, said gaze tracking device tracking attributes of a viewing behavior of one or more first expert users when performing a task and storing said attributes of said viewing behavior in a memory storage device associated with a processor device, said attributes of viewing behavior comprising a user's gaze pattern including: locations where a viewing gaze is fixated, a gaze duration at said locations, a gaze path being tracked, and a location representing a weighted average of a plurality of gaze positions whose weights are associated with corresponding time values; and said gaze tracking device further tracking said attributes of a viewing behavior of one or more second novice users when performing the task and storing said attributes of said novice user's viewing behavior in a memory storage device associated with a processor device;

wherein the at least one processor is further configured to:

implement a machine learning algorithm to learn differences between said attributes of viewing behavior of said one or more first expert users performing said task and said attributes of viewing behavior of said one or more second novice users performing the task and associate said learned differences with significant positive or negative outcomes of said task;

store in said memory storage device a catalog of said learned differences for the task that are tied to said significant outcomes; and subsequently track, using said gaze tracking device, a further user's viewing behavior when subsequently performing the same task as said one or more first expert users;

compare, in real time, attributes of said further user's viewing behavior with said stored attributes of said first expert user's behavior tied to said significant outcomes to detect real-time viewing behavior differences;

compare, in real time, a detected difference against said catalog of stored learned differences that are tied to said significant outcomes; and provide an output indication for said further user to correct any said detected behavioral differences commensurate with said significant outcomes such that said further user acquires skills as said first expert user.

6. The system according to claim 5, wherein performing a task comprises viewing an image through a user interface.

7. The system according to claim 5, wherein said memory storage comprises a database device in which said detected differences are catalogued.

8. The system according to claim 5, wherein the processor is configured to provide an indication to correct detected behavioral differences and further configured to perform creating movement of a displayed image via said interface, changing color of said image via said interface or changing intensity of said image via an interface to align second reference patterns with first reference patterns, or combinations thereof.

9. A computer program product comprising at least one non-transitory computer usable medium having computer readable program code logic to execute a machine instruction in a processing unit for controlling skill acquisition interfaces, said computer readable program code logic when executed by said processing unit performing steps to:

track, using a gaze tracking device having a lens for real-time video capture, attributes of a viewing behavior of one or more first expert users when performing a task and storing said attributes of said viewing behavior in a memory storage device associated with a processor device, said attributes of viewing behavior comprising a user's gaze pattern including: locations where a viewing gaze is fixated, a gaze duration at said locations, a gaze path being tracked, and a location representing a weighted average of a plurality of gaze positions whose weights are associated with corresponding time values;

track, using said gaze tracking device, said attributes of a viewing behavior of one or more second novice users when performing the task and storing said attributes of said novice user's viewing behavior in a memory storage device associated with a processor device;

implement a machine learning algorithm to learn differences between said attributes of viewing behavior of said one or more first expert users performing said task and said attributes of viewing behavior of said one or more second novice users performing the task and associating said learned differences with significant positive or negative outcomes of said task;

store in said memory storage a catalog of said learned differences for the task that are tied to said significant outcomes; and subsequently track, using said gaze tracking device, a further user's viewing behavior when subsequently performing the same task as said one or more first expert users;

compare, in real time, attributes of said further user's viewing behavior with said stored attributes of said first expert user's behavior tied to said significant outcomes to detect real-time viewing behavior differences;

compare, in real time, a detected difference against said catalog of stored learned differences that are tied to said significant outcomes; and provide an output indication for said further user to correct any said detected behavioral differences commensurate with said significant outcomes such that said further user acquires skills as said first expert user.

10. The computer program product according to claim 9, wherein performing a task comprises viewing an image through a user interface.

11. The computer program product according to claim 9, wherein said differences are catalogued into a database.

12. The computer program product according to claim 9, wherein the step of correcting differences comprises one of: creating movement of a displayed image, changing color of said image and changing intensity of said image.

* * * * *